United States Patent [19]

Medel

[11] 4,402,686

[45] Sep. 6, 1983

[54] PINCHED NERVE INSTRUMENT

[76] Inventor: Gonzalo A. Medel, Box 622, Round Rock, Tex. 78664

[21] Appl. No.: 281,679

[22] Filed: Jul. 9, 1981

[51] Int. Cl.[3] ........................................ A61M 35/00

[52] U.S. Cl. ........................................ 604/311

[58] Field of Search ............... 128/276, 277, 278, 280, 128/281, 282, 297-302, 205.18; 417/437; 92/13.8; 172/464, 466; 305/10; 604/310, 311

[56] References Cited

U.S. PATENT DOCUMENTS

| | | | |
|---|---|---|---|
| 790,051 | 5/1905 | Halstead | 128/281 |
| 798,893 | 9/1905 | Ezel | 128/281 |
| 2,580,169 | 12/1951 | Golden et al. | 604/311 |
| 2,591,443 | 4/1952 | Larson et al. | 128/300 |
| 3,008,772 | 11/1961 | Helsel, Sr. | 305/10 |
| 3,815,480 | 6/1974 | Spyra | 92/13.8 |
| 4,221,550 | 9/1980 | Pleass | 417/437 |

FOREIGN PATENT DOCUMENTS

| | | | |
|---|---|---|---|
| 160945 | 7/1953 | Australia | 128/281 |
| 12612 | of 1849 | United Kingdom | 128/281 |

*Primary Examiner*—Richard J. Apley
*Assistant Examiner*—J. L. Kruter

[57] ABSTRACT

This instrument is for relieving a pinched muscle on the spine of a patient, and it consists primarily of a glass bell member for placement on the injured area adjacent to the spine. It further includes a sleeve secured to the bell, which receives a threaded rod and a rubber ball, which serve as piston and rod means, for creating a suction, to relieve pain in the injured area. The rod further includes nuts and a removable clamp, for adjustment of the instrument.

1 Claim, 2 Drawing Figures

PINCHED NERVE INSTRUMENT

This invention relates to medical instruments, and more particularly, to a pinched nerve instrument.

The term "pinched nerve" usually refers to a contracted muscular spasm in which the muscular nerves can cause a severe, long-lasting pain. Heretofore, it was often treated by heat applications or by massages so as to relax the muscles. It has also been found that the application of a suction force against a skin surface of a person forms a type of massage that additionally strongly stimulates a blood circulation through the adjacent affected area, while not harming a derma or subcutaneous cellular tissue when the suction is of proper force and not excessive.

It is the principal object of this invention to provide a pinched nerve instrument, which will effectively relieve a pinched muscle in the spinal area.

Another object of this invention is to provide a pinched nerve instrument, which will be of such structure, as to employ suction as a means for relieving a pinched muscle.

A further object of this invention is to provide a pinched nerve instrument, which will be adjustable by clamp and nut fastener means.

Other objects are to provide a pinched nerve instrument, which is simple in design, inexpensive to manufacture, rugged in construction, easy to use, and efficient in operation.

Figure 1:
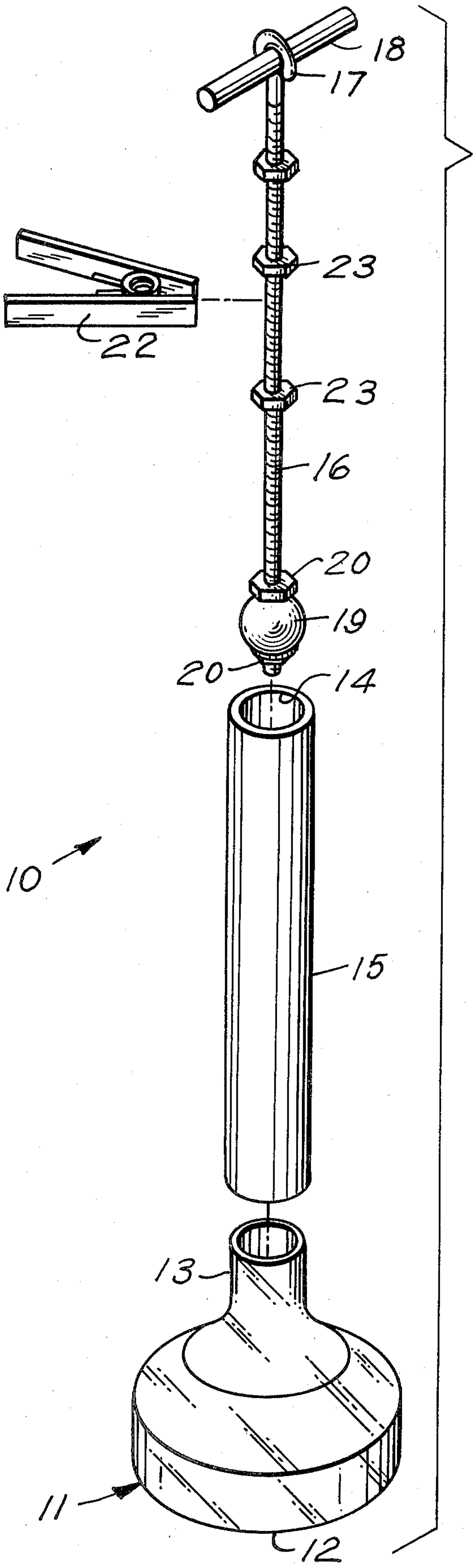
Figure 2:
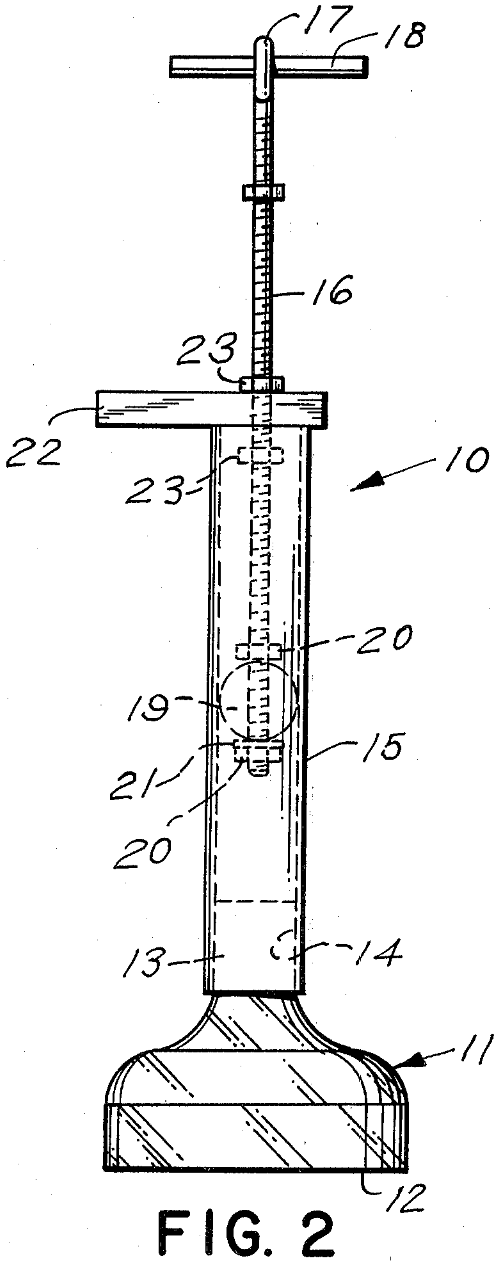

These, and other objects, will be readily evident, upon a study of the following specification, and the accompanying drawing, wherein:

FIG. 1 is a partially exploded perspective view of the present invention, and FIG. 2 is a side elevational view of the assembled structure of FIG. 1.

According to this invention, instrument 10 is shown to include a glass bell 11, the peripheral rim 12 being smooth, so as not to injure the skin of the patient, when instrument 10 is in use. The neck portion 13 of bell 11 is frictionally, or otherwise, secured within one end of the bore 14 of a chromed metal sleeve 15. An externally threaded rod 16 includes a hook 17 at one end, which receives a wooden handle 18, for operating rod 16. A rubber ball 19 is received on the opposite end of rod 16, and is held in position by means of a pair of nut fasteners 20. The nut fasteners 20 also enable adjustment of the ball 19 for proper suction, and a rubber washer 21 is received on rod 16, against the ball 19 and the bottom fastener 20. A spring clamp 22, of common construction, is removably received on rod 16, between plural nut fasteners 23, so as to keep the rod 16 in its proper place, once the instrument is in use.

In use, warm pads are used on the injured area for ten or fifteen minutes, after which, the bell 11 is placed with its peripheral rim 12 on the side of the injured area (never directly on the spine or other organ). The rod 16 is then placed in the sleeve 15, and is pulled upwards by the handle 18, until a suction is created, to a degree that will not cause further injury to the area. The clamp 22 is then put in place between the fasteners 23, so as to hold rod 16 in place. The user then massages the spine lightly, for two or three minutes, and then releases the suction, by pushing rod 16 downwards a little, whereupon, the suction is lost. Instrument 10 is used once daily, as needed, and it is to be noted, that the ball 19 serves as piston means for creating the suction within the bore 14 of sleeve 15, and the interior of the bell 11.

While various changes may be made in the detail construction, it is understood that such changes will be within the spirit and scope of the present invention, as is defined by the appended claims.

What I now claim is:

1. An instrument to relieve pinched nerves, comprising, in combination, a glass bell, a tubular, cylindrically-shaped metal sleeve, said bell being tubular, with one end thereof having a wide mouth, while an opposite end thereof forms a narrow neck frictionally secured inside one end of said sleeve; a threaded rod inserted through an opposite end of said sleeve, a rubber ball fitted on one end of said rod that is inside said sleeve, said ball being of a size so as to frictionally slide inside said sleeve when said rod is axially moved relative to said sleeve, a rubber washer on said rod and adjacent one side of said ball, a pair of nut fasteners engaged on said rod, one said nut fastener being adjacent an opposite side of said ball while the other said nut fastener is adjacent said washer; a hook formed on an opposite end of said rod and a wooden handle inserted in said hook, a plurality of other nut fasteners engaged in spaced-apart relation along an intermediate portion of said rod forming a plurality of adjustable spaces therebetween and a spring clamp engaging said rod in selected of said spaces formed between said other nut fasteners, said spring clamp extending transversely a greater distance than a width of said sleeve so as to abut against said opposite end thereof.

* * * * *